(12) United States Patent
Mascarenhas Saraiva et al.

(10) Patent No.: US 7,265,245 B2
(45) Date of Patent: Sep. 4, 2007

(54) COMPOUNDS USEFUL FOR THE TREATMENT OF DISEASES ASSOCIATED WITH THE FORMATION OF AMYLOID FIBRILS

(75) Inventors: Maria Joao Mascarenhas Saraiva, Oporto (PT); Maria do Rosario Rodrigues Almeida, Oporto (PT); José Barluenga Mur, Oviedo (ES); Alfredo Ballesteros Gimeno, Oviedo (ES); Antoni Planas Sauter, Barcelona (ES); Gemma Arsequell Ruiz, Barcelona (ES); Gregorio Valencia Parera, Barcelona (ES)

(73) Assignee: Innovaprotean, S.L, Barcelona (ES)

( * ) Notice: Subject to any disclaimer, the term of this patent is extended or adjusted under 35 U.S.C. 154(b) by 0 days.

(21) Appl. No.: 10/574,875

(22) PCT Filed: Oct. 8, 2003

(86) PCT No.: PCT/ES03/00510

§ 371 (c)(1),
(2), (4) Date: Dec. 6, 2006

(87) PCT Pub. No.: WO2005/033059

PCT Pub. Date: Apr. 14, 2005

(65) Prior Publication Data

US 2007/0167378 A1    Jul. 19, 2007

(51) Int. Cl.
*C07C 233/65*    (2006.01)
*A61K 31/165*    (2006.01)

(52) U.S. Cl. .................. 564/171; 514/532; 514/563; 514/568; 514/617; 560/57; 562/444; 562/469; 536/6.5; 536/4.1

(58) Field of Classification Search .......... 514/532, 514/563, 568, 617; 564/171; 560/57; 562/444; 562/469; 536/4.1, 6.5
See application file for complete search history.

(56) References Cited

FOREIGN PATENT DOCUMENTS

| EP | 0082404 A1 | 8/1983 |
|---|---|---|
| FR | 1405542 * | 5/1965 |
| WO | WO --98/20884 A2 | 5/1998 |
| WO | WO --98/46234 A1 | 10/1998 |

* cited by examiner

*Primary Examiner*—Shailendra Kumar
(74) *Attorney, Agent, or Firm*—Steven J. Hulquist; Intellectual Property/ Technology Law

(57) ABSTRACT

The present invention provides new amyloidogenesis inhibiting compounds of formula (I):

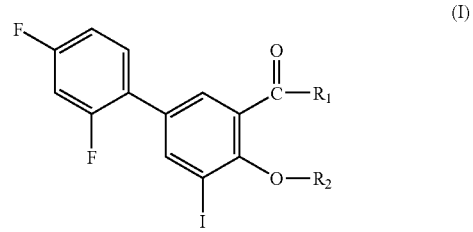

(I)

in which
R$_1$ is a —NR$_a$R$_b$ group, where R$_a$ and R$_b$, independently, are a hydrogen atom or a C$_1$-C$_6$ alkyl group; —OR$_C$ group, where R$_C$ is a hydrogen atom or a C$_1$-C$_6$ alkyl group; a glycosyl; a C$_1$-C$_6$ polyhydroxyalkyl; or a —NH—CH(R$_d$)—COOR$_e$ group, where R$_d$ is a side chain of one of the 20 natural alpha-amino acids in either of their two enantiomerically pure forms L or D, and R$_e$ is a hydrogen atom or a C$_1$-C$_6$ alkyl group; and
R$_2$ is a hydrogen atom, a C$_1$-C$_6$ alkyl group, a glycosyl; a C$_1$-C$_6$ polyhydroxyalkyl; —C(=O)—R$_f$ group, where R$_f$ is a C$_1$-C$_6$ alkyl group; or a —CH$_2$—COO—R$_g$ group, where R$_g$ is a hydrogen atom or a C$_1$-C$_6$ alkyl group;
and pharmaceutically acceptable salts thereof, which are useful in the treatment of neurodegenerative diseases, among others.

6 Claims, 1 Drawing Sheet

US 7,265,245 B2

COMPOUNDS USEFUL FOR THE TREATMENT OF DISEASES ASSOCIATED WITH THE FORMATION OF AMYLOID FIBRILS

This application is a 371 of PCT/ES03/00510, filed Oct. 8, 2003.

FIELD OF THE INVENTION

The present invention refers to the field of the treatment of amyloid diseases, in particular to amyloidogenesis inhibitor agents and, more specifically, to compounds that inhibit the formation of amyloid fibrils associated with transthyretin. Similarly, the invention also refers to the use of these compounds for the treatment of diseases associated with amyloid fibril formation, mainly neurodegenerative diseases.

PRIOR ART

A common feature of amyloid neurodegenerative diseases is the deposition of high molecular weight fibrils with a cross beta-sheet structure on the basis of the self-assemblage of one of the approximately twenty human proteins whose involvement in this type of condition is known (Kelly, J. W. Curr. Op. Struct. Biol., 6 (1996) 11; Kelly, J. W. Structure, 5 (1997) 595; Kelly, J. W. Curr. Op. Struct. Biol., 5 (1998) 101; Lansbury, P. T. Biochemistry, 31 (1992) 6865; Sipe, J. D. Ann. Rev. Biochem., 61 (1992) 947; Sipe, J. D. Crit. Rev. in Clin. Lab. Sci., 31 (1994) 325; y Blake, C., Serpell, L. Structure, 4 (1996) 989).

In the specific case of transthyretin (TTR), which is comprised in the above-mentioned group of amyloid proteins, the deposition of fibrils of native variant fibrils which infiltrate in the heart appear to be the cause of senile systemic amyloidosis (cardiomyopathy) (Cornwell, G. C., et al., Biochem. Biophys. Res. Commun., 154 (1988) 648). Analogously, the deposition in a single residue of one of the 60 known mutants that make TTR more amyloidogenic appears to be associated with a series of alterations that are referred to collectively as familial amyloid polyneuropathies (Jacobson, D. R., et al. Adv. Human Genetics, 20 (1991) 69). Unlike other neurodegenerative syndromes, these diseases do not affect the brain but they do affect certain organs and the peripheral nervous system. Thus, patients affected by these familial diseases present peripheral neuropathies and/or organic dysfunctions caused by amyloid neurotoxicity and/or physical interference with the normal working of vital organs which are manifested as early as the age of 20 years. At the present time, no pharmacological treatment exists or has been proposed for this kind of amyloid diseases, and the only effective therapeutic measure available is liver transplant, as this is the organ where transthyretin is biosynthesized.

The amyloid diseases associated with transthyretin were some of the first in which it was discovered that they evolve through the formation of fibrils originated by a conformational change in a specific protein. In its natural form, TTR is organized as a tetramer that is possibly dissociated in its monomers, which are capable of self-associating in fibrils 130 Å in diameter, in turn composed of protofilaments, each formed of a folded cross beta-sheet structure (Serpell L. C. et al. J. Mol. Biol., 254 (1995) 113; y Kelly J. W., et al., Adv. Protein Chem., 50, 161). This knowledge at molecular level of the formation of TTR fibrils has been possible thanks to the fact that this amyloidosis has been successfully studied in vitro as the acid medium is a natural trigger for the process (Colon, W., et al. in *Transthyretin acid induced denaturation is required for amyloid fibril formation in vitro*. Eds., Plenum Press, New York, 1991, p 99). Thus, by means of partial acid TTR denaturation experiments simulating the conditions present in the lysosome (pH: 5.5), it has been concluded that the fibrils are generated from conformational intermediates (amyloidogenic intermediate) of the monomeric units of transthyretin. This research has confirmed that TTR is not amyloidogenic in tetrameric form, but dissociation of the tetramer into a monomer with an altered but defined tertiary structure is what gives rise to the formation of fibrils (Lai, Z., et al., J. W. Biochemistry, 35 (1996) 6470; and Quintas, A., et al., J. Biol. Chem., 274 (1999) 32943).

Transthyretin, also known as prealbumin, is present in human plasma (3.6 µM) and in cerebrospinal fluid. It is composed of 4 identical peptide chains of 127 amino acids rich in beta structure forming a dimer of dimers whose mass is 55 kDa and whose structure is known through x-ray diffraction (Blake, C. C. F., et al., J. Mol. Biol., 121 (1978) 339; and Hamilton, J. A., et al., J. Biol. Chem., 268 (1993) 2416). This tetramer binds and transports the hormone thyroxine and the retinol binding protein. X-ray diffraction studies have also revealed that TTR presents two binding sites for thyroxine which are funnel-shaped and are well defined by the dimer-dimer interfaces (Wojtczak, A., et al., J. Biol. Chem., 267 (1992) 353; and Wojtczak, A., et al., Acta Cryst., D52 (1996) 758). In other words, every tetramer can bind to two thyroxine molecules. This binding shows negative cooperativeness for the entry of the second ligand molecule.

It has recently been shown that the tetrameric form of TTR may be stabilized against the amyloidogenesis-inducing acid medium by means of binding to small organic molecules that mimic the structure of the natural ligand. The evidence that these ligands prevent the formation of fibrils comes from in vitro and ex vivo experiments only. These molecules include such non-steroidal anti-inflammatory molecules as flufenamic acid (Peterson, S. A., et al., Proc. Natl. Acad. Sci. USA, 95 (1998) 12956) and diflunisal (Baures, P. W., et al., J. W. Bioorg. Med. Chem., 7 (1999) 1339), as well as molecules of a series of active ingredients of drugs, including flavones, tetrahydroquinolines, dihydropyridines and benzodiazepines (Baures, P. W., et al., Bioorg. Med. Chem., 6 (1998) 1389), besides derivatives of anthranilic acid (Oza, V. B., et al. Bioorg. Med. Chem. Lett., 9 (1999) 1).

In a purely empirical and intuitive way, these studies have succeeded in clarifying some structural requirements that the TTR tetramer dissociation inhibitors must have, which may be summarized as follows:

Biphenyl, dibenzofurane, diaryl ether, stilbene and flavone structures may be accommodated at the binding site (Baures, P. W., et al., J. W. Bioorg. Med. Chem., 6 (1998) 1389). Flufenamic acid analogues with an anthranilic acid structure are also good inhibitors (Oza, V. B., et al., Bioorg. Med. Chem. Lett., 9 (1999) 1). In general, it seems that the pharmacophore has to have two aromatic rings, one of which may be bi- or tricyclic. One of the rings or fusion of rings would occupy the outer part of the binding site (Baures, P. W., et al., Bioorg. Med. Chem., 7 (1999) 1339).

The presence of a carboxylic acid group possibly optimizes the binding to TTR via interaction with the Lys residue(s) in position 15 (Baures, P. W., et al., J. W.

Bioorg. Med. Chem., 6 (1998) 1389). This acid group may also be a phenol (Baures, P. W., et al., Bioorg. Med. Chem., 7 (1999) 1339).

The search for TTR dissociation inhibitors set under way by means of these initial studies has not been systematic and it has only been discovered that flufenamic acid is a good inhibitor. Thus, for example, 79 compounds have been tested, as described in Baures et al., Bioorg. Med. Chem., 6 (1998) 1389, and in Baures, P. W., et al., Bioorg. Med. Chem., 7 (1999) 1339, all of them of commercial origin. A series of products have also been synthesized (Oza, V. B., Petrassi H. M., Purkey H. E., Kelly, J. W. Bioorg. Med. Chem. Lett., 9 (1999) 1) on the basis of the structural data obtained by means of x-ray diffraction analysis of the TTR complex and flufenamic acid (Peterson, S. A., Klabunde, T., Lashuel, H. A., Purkey, H., Sacchettini, J. C., Kelly, J. W. Proc. Natl. Acad. Sci. USA, 95 (1998) 12956).

Likewise, in the international patent application WO 98/27972 compounds are described that stabilize an amyloidogenic protein as TTR by means of the formation of a protein-drug conjugate. Amongst these compounds non-steroidal anti-inflammatory compounds (NSAIs) are mentioned and, amongst these, diflunisal. Such NSAIs as ibuprofen, indomethacin and sulindac sulphide have also been put forward and they continue to be researched as potential therapeutic agents for the amyloidosis processes that occur in Alzheimer's disease (S. Wegen et al. Nature, 414 (2001) 212-216)

The use of diflunisal, amongst other NSAIs, as a selective TTR ligand has already been described in American patent U.S. Pat. No. 5,714,142; in this case to extend the half-life in serum of pharmacologically active agents.

However, the use of diflunisal to stabilize the tetrameric structure of TTR and, therefore, for the treatment of neurodegenerative diseases associated with the formation of amyloid fibrils continues to present a series of drawbacks characteristic of the NSAIs, such as gastrointestinal and cardiovascular side effects.

There is, therefore, a continuing need in the state of the art to provide alternative TTR dissociation inhibitors more effective and with fewer side effects.

Surprisingly, the present authors have discovered that a series of iodinated derivatives of diflunisal are potent anti-amyloidogenic agents with an efficacy superior to that of diflunisal and, therefore, with fewer side effects than the latter, through being able to be administered in smaller doses.

Hitherto, no iodinated diflunisal derivatives have been described in the salicylic ring. European patent EP 0082404 discloses a series of ester diflunisal derivatives, useful as anti-inflammatories, analgesics and antipyretics, but the above-mentioned iodinated derivatives are not included amongst them.

The object of the present invention, therefore, is to provide potent amyloidogenesis inhibiting agents, more effective and with fewer side effects.

OBJECT OF THE INVENTION

One object of the present invention is to provide new amyloidogenesis inhibiting compounds.

Another object of the present invention is to provide a method for the preparation of these compounds.

Another object of the present invention is to provide a pharmaceutical composition containing these compounds.

Lastly, another object of the present invention is to provide the therapeutic use of these compounds in the treatment of neurodegenerative diseases and other diseases.

DETAILED DESCRIPTION OF THE INVENTION

Figure 1:
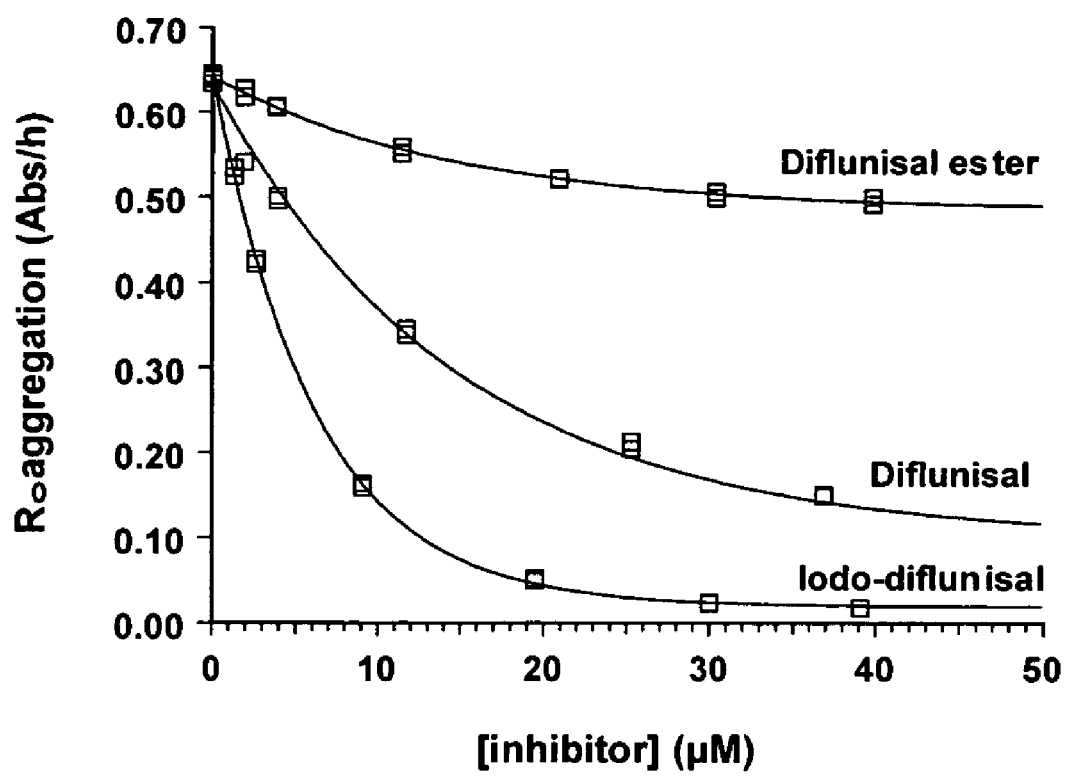
FIG. 1 shows a graph representing the aggregation rate, $v_0$, versus inhibitor concentration, [I], for a compound of the invention, iododiflunisal, in respect of two conventional compounds, diflunisal and diflunisal ester.

The invention provides a compound of structural formula (I):

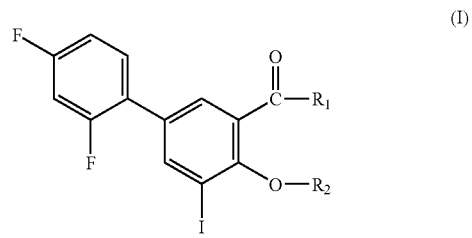

in which
$R_1$ is a —$NR_aR_b$ group, where $R_a$ and $R_b$, independently, are a hydrogen atom or a $C_1$-$C_6$ alkyl group; a —$OR_C$ group, where $R_C$ is a hydrogen atom or a $C_1$-$C_6$ alkyl group; a glycosyl; a $C_1$-$C_6$ polyhydroxyalkyl; or a —NH—CH($R_d$)—COOR$_e$ group, where $R_d$ is a side chain of one of the 20 natural alpha-amino acids in either of the two enantiomerically pure forms L or D, and $R_e$ is a hydrogen atom or a $C_1$-$C_6$ alkyl group; and
$R_2$ is a hydrogen atom, a $C_1$-$C_6$ alkyl group; a glycosyl; a $C_1$-$C_6$ polyhydroxyalkyl; a —C(=O)—$R_f$ group, where $R_f$ is a $C_1$-$C_6$ alkyl group or a —$CH_2$—COO—$R_g$ group, where $R_g$ is a hydrogen atom or a $C_1$-$C_6$ alkyl group;

and pharmaceutically acceptable salts thereof.

In the present invention, the term "glycosyl group" refers to a radical obtained by elimination of an OH group from the hemiacetal function of a monosaccharide, i.e. a group of formula $C_6H_{11}O_5$ or $C_6H_{10}O_6$. Similarly, the term "$C_1$-$C_6$ polyhydroxyalkyl group" refers to an alkyl group substituted by various OH groups.

In a preferred embodiment, the compounds of the invention are compounds of formula (i) in which $R_1$ is selected from: OH, $NH_2$, OMe, OEt, or a CH($R_d$)—COOR$_e$ group, where $R_d$ is the side chain of glycine, alanine, leucine, valine, aspartic acid or asparagine and where $R_e$ is H or a $C_1$-$C_6$ alkyl group; and $R_2$ is selected from: H, Me, glycosyl, a —C(=O)—$R_f$ group, where $R_f$ is a Me, Et, t-Bu group; or a —$CH_2$—COO—$R_g$ group, where $R_g$ is a hydrogen atom or a t-Bu group.

In another preferred embodiment of the present invention, the compounds of formula (I) are selected from the following compounds:

[1] 5-(2,4-difluorophenyl)-3-iodo-salicylic acid;
[2] ethyl 5-(2,4-difluorophenyl)-3-iodo-salicylate;
[3] methyl 5-(2,4-difluorophenyl)-3-iodo-salicylate;
[4] 5-(2,4-difluorophenyl)-3-iodo-salicylamide;

[5] tert-butyl [2-aminocarbonyl-4-(2,4-difluorophenyl)-6-iodo-phenoxy]-acetate;
[6] [2-aminocarbonyl-4-(2,4-difluorophenyl)-6-iodo-phenoxy]acetic acid;
[7] 5-(2,4-difluorophenyl)-3-iodo-salicylic acid 1-O-glycoside;
[8] ethyl 2',4'-difluoro-4-methoxy-5-iodo-[1,1']biphenyl-3-carboxylate;
[9] 2',4'-difluoro-4-methoxy-5-iodo-[1,1']biphenyl-3-carboxylic acid;
[10] ethyl 2',4'-difluoro-4-acetyloxy-5-iodo-[1,1']biphenyl-3-carboxylate;
[11] 2',4'-difluoro-4-(t-butylcarbonyloxy)-5-iodo-[1,1']biphenyl-3-carboxylic acid;
[12] 2',4'-difluoro-4-(ethylcarbonyloxy)-5-iodo-[1,1']biphenyl-3-carboxylic acid;
[13] ethyl ester of N-[5-(2,4-difluorophenyl)-3-iodo-salicyloyl]glycine;
[14] N-[5-(2,4-difluorophenyl)-3-iodo-salicyloyl]glycine;
[15] N-[5-(2,4-difluorophenyl)-3-iodo-salicyloyl]alanine;
[16] N-[5-(2,4-difluorophenyl)-3-iodo-salicyloyl]leucine;
[17] N-[5-(2,4-difluorophenyl)-3-iodo-salicyloyl]serine;
[18] N-[5-(2,4-difluorophenyl)-3-iodo-salicyloyl]valine;
[19] N-[5-(2,4-difluorophenyl)-3-iodo-salicyloyl]-aspartic acid;
[20] N-[5-(2,4-difluorophenyl)-3-iodo-salicyloyl]asparagine.

Another object of the present invention is to provide a method for the preparation of the compounds of formula (I), characterised in that it comprises a step of reacting diflunisal or derivatives thereof with an iodination reagent.

Iodination of diflunisal or of diflunisal derivatives is obvious for a skilled person in the art, who will select the starting compound and iodination reagent accordingly. Similarly, the preparation of diflunisal derivatives (esters, carboxamides, salts, glycosides, amino acid derivatives, etc.) will be obvious for the skilled person. Furthermore, the iodination reagent may be selected from: elemental iodine; iodide salts such as sodium iodide or potassium iodide; iodonium salts such as iodine chloride; iodonium complexes such as bis(pyridine)iodonium (I) tetrafluoroborate or bis(sym-collidine)iodonium (I) hexafluorophosphate; and organic iodine compounds, such as iodobenzene diacetate or N-iodosuccinimide.

Likewise, another object of the present invention is to provide a pharmaceutical composition that contains a compound of the invention and one or more pharmaceutically acceptable excipients.

Pharmaceutically acceptable excipients will be those excipients known in the art that permit the suitable formulation of the pharmaceutical composition of the invention. This composition may be formulated for oral, intravenous, topical, rectal, subdermal, etc. administration. In other words, it may be in the form of solutions, tablets, capsules, implants, etc. This formulation may also be the immediate- or controlled-release type.

In any case, the physician will be the one to decide the most suitable dosage in accordance with the patient's age, general state of health, weight and the type or extent of the disease or disorder to be treated.

An additional object of the present invention is to provide the compounds of the invention for the treatment of neurodegenerative diseases, including amyloid neurodegenerative diseases, such as Alzheimer's disease, Parkinson's disease, Huntington's disease, Creutzfeldt-Jakob disease, cystic fibrosis, late-onset diabetes, motor neuron disease, Mediterranean fever, Muckle-Wells syndrome, idiopathic myeoloma, amyloid cardiopathy, Down's syndrome, Kuru disease, Gerstmann-Straussler-Schienker syndrome, amyloid valvular deposits, amyloidosis in dialysis patients, inclusion body myositis, amyloid muscular deposits, Sickle Cell anemia, primary systemic amyloidosis, senile systemic amyloidosis, familial amyloid polyneuropathy I, familial amyloid polyneuropathy III, hereditary cerebral amyloid angiopathy, angiopathy-related amyloidosis, Finnish hereditary systemic amyloidosis, type II diabetes, medullar thyroid carcinoma, spongiform encephalopathy, atrial amyloidosis, hereditary non-neuropathic systemic amyloidosis, injection-localized amyloidosis, and hereditary renal amyloidosis.

In a preferred embodiment of the present invention, the compounds of the invention may also be used as analgesic, anti-inflammatory, antipyretic or platelet anti-aggregatory drug for the treatment of such diseases as rheumatoid arthritis, rheumatoid fevers, osteoarthritis, musculoskeletal pains, inflammatory bowel disease, coronary artery diseases or postoperative deep vein thrombosis.

The following examples set out to illustrate the invention.

EXAMPLES OF PREPARATION

Example 1

5-(2,4-difluorophenyl)-3-iodo-salicylic acid

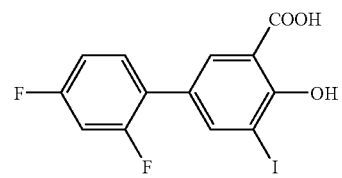

By iodination of 5-(2,4-difluorophenyl)salicylic acid (diflunisal) with the reagent bis(pyridine)iodonium (I) tetrafluoroborate ($Ipy_2BF_4$)

357 mg (1.2 mmol) of $Ipy_2BF_4$ was added to a solution of 200 mg (0.80 mmol) of diflunisal in 5 ml of dichloromethane at room temperature. It was stirred until the consumption of starting product was observed by HPLC (high performance liquid chromatography). It was diluted in dichloromethane and the product was worked up by acidification with 1 N HCl acid and extraction with dichloromethane. The organic phases were combined and washed with a solution of sodium thiosulphate and then dried over anhydrous magnesium sulphate. The solvent was removed at low pressure and a crude of 98% purity was obtained and then purified by chromatography on silica gel. 290 mg (96% yield) of the desired product was obtained.

Example 2

5-(2,4-difluorophenyl)-3-iodo-salicylic acid

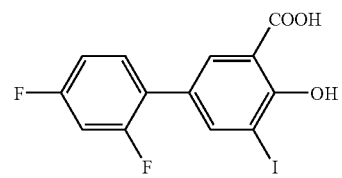

By iodination of 5-(2,4-difluorophenyl)salicylic acid (diflunisal) with the reagent bis(2,4,6-trimethylpyridine)iodonium hexafluorophosphate (I) (IColl$_2$ PF$_6$)

617 mg (1.2 mmol) of IColl$_2$PF$_6$ was added to a solution of 200 mg (0.80 mmol) of diflunisal in 5 ml of dichloromethane at room temperature. It was stirred until the consumption of starting product was observed by HPLC. It was diluted in dichloromethane and the product was worked up by acidification with 1 N HCl acid and extraction with dichloromethane. The organic phases were combined and washed with a solution of sodium thiosulphate and then dried over anhydrous magnesium sulphate. The solvent was removed at low pressure and a crude of 98% purity was obtained and then purified by chromatography on silica gel. 260 mg (86% yield) of the desired product was obtained.

Example 3

5-(2,4-difluorophenyl)-3-iodo-salicylic acid

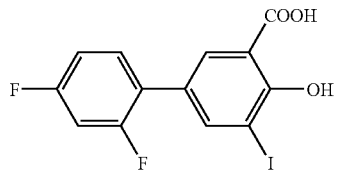

By iodination of 5-(2,4-difluorophenyl)salicylic acid (diflunisal) with chloramine-T (CAT) and sodium iodide.

20 mg (0.08 mmol) of diflunisal, 14 mg (0.093 mmol) of NaI and 30 mg (0.13 mmol) of CAT dissolved in 1040 µl of acetonitrile and 52 µl of acetic acid are placed in a 25 ml flask. It was stirred for 1.5 hr at room temperature. The reaction was monitored by HPLC until the consumption of starting product was observed and 96% of iodinated product was detected. The solution was then acidified to pH=1.0 with a 5% solution of HCl and extracted with ethyl acetate. The organic phases were combined and washed with a solution of sodium thiosulphate and then dried over anhydrous magnesium sulphate. The solvent was removed at low pressure and a crude of 98% purity was obtained and then purified by chromatography on silica gel. 260 mg (86% yield) of the desired product was obtained.

Example 4

5-(2,4-difluorophenyl)-3-iodo-salicylic acid

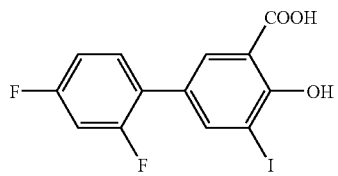

By iodination of 5-(2,4-difluorophenyl)salicylic acid (diflunisal) with sodium iodide and sodium hypochlorite An equivalent of sodium iodide (165 mg, 1.1 mmol) and an equivalent of sodium hydroxide (32 mg) were added to a solution of 200 mg (0.80 mmol) of diflunisal in 5 ml of methanol. A 4% solution of sodium hypochlorite was dropwise added to the previous solution over a period of 75 min, keeping the temperature at 0-3° C. After every addition, a reddish colour was observed which quickly disappeared. It was stirred at this temperature for another hour and treated with a 20% aqueous solution of sodium thiosulphate. A 5% solution of HCl was added and it was extracted with dichloromethane. After the work-up, the product was recrystalized.

Example 5

5-(2,4-difluorophenyl)-3-iodo-salicylic acid

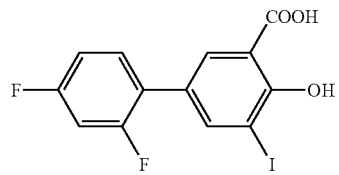

By iodination of 5-(2,4-difluorophenyl)salicylic acid (diflunisal) with iodine chloride (ICl).

195 mg (1.2 mmol) of ICl in dichloromethane (1 M) was added at room temperature to a solution of 200 mg (0.80 mmol) of diflunisal in 5 ml of dichloromethane. It was stirred continuously at room temperature for 3 hr and the product was then worked up, as described in example 1.

Example 6

5-(2,4-difluorophenyl)-3-iodo-salicylic acid

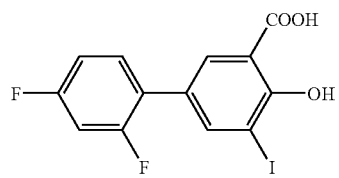

By iodination of 5-(2,4-difluorophenyl)salicylic acid (diflunisal) with iodine and Selectfluor™.

200 mg (0.80 mmol) of diflunisal was added to a solution of 354 mg (1 mmol) of Selectfluor™ and 127 mg (0.5 mmol) of iodine in 10 ml of acetonitrile and the reaction was stirred at room temperature for 3 hr. It was treated with a 20% aqueous solution of sodium thiosulphate. A 5% solution of HCl was added and it was extracted with dichloromethane. After the work-up, the product was recrystalized.

Example 7

5-(2,4-difluorophenyl)-3-iodo-salicylic acid

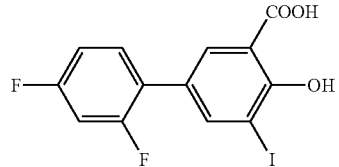

By iodination of 5-(2,4-difluorophenyl)salicylic acid (diflunisal) with N-iodosuccinimide (NIS).

198 mg (0.88 mmol, 1.1 eq) of NIS was added at room temperature to a solution of 200 mg (0.8 mmol) of diflunisal in 4 ml of acetonitrile and a catalytic quantity of 18 μl (0.24 mmol, 0.3 eq) of trifluoroacetic acid. It was stirred continuously. The solvent was evaporated at low pressure, it was diluted with dichloromethane and the product was then worked up as in example 1.

Example 8

5-(2,4-difluorophenyl)-3-iodo-salicylic acid

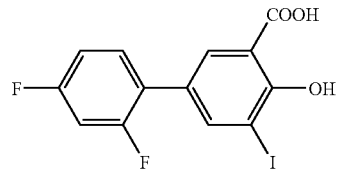

By iodination of 5-(2,4-difluorophenyl)salicylic acid (diflunisal) with thallium trifluoroacetate and potassium iodide.

A mixture of 20.6 g of thallium trifluoroacetate (TTFA, 31.9 mmol) and trifluoroacetic acid (TFA, 50 ml) was stirred in a flask until the TTFA dissolved. This solution was added at room temperature to a flask containing 51 g (205 mmol) of diflunisal and it was stirred for 30 min. A solution of potassium iodide (KI, 40.9 g, 245.6 mmol) in 120 ml of water was slowly added to the mixture. After the reaction finished, the product was worked up. First, sodium metabisulphite ($NaS_2O_5$, 5.01 g, 26.4 mmol) was added to reduce the species of TI (III) to TI (I), and then a solution of sodium hydroxide was added to neutralize the TFA. It was extracted with dichloromethane and the organic phase was washed with water and dried over magnesium sulphate. The solvent was evaporated at low pressure and a crude was obtained of 96% purity, which was purified by chromatography on a silica gel column using the appropriate eluents.

Example 9

Ethyl 5-(2,4-difluorophenyl)-3-iodo-salicylate

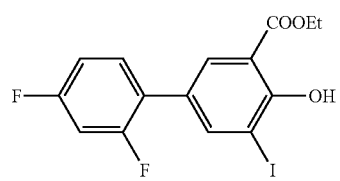

11.5 ml of ethyl alcohol and 2.9 ml of thionyl chloride ($SOCl_2$) were placed in a flask under an inert atmosphere. It was stirred for 15 min and 1.67 g (4.56 mmol) of 5-(2,4-difluorophenyl)-3-iodo-salicylic acid was added. It was stirred continuously at room temperature until no evolution was observed by HPLC. The solvent was evaporated at low pressure and extracted with ethyl acetate. A crude of 97% purity was obtained and then purified by chromatography on silica gel.

Example 10

Ethyl 5-(2,4-difluorophenyl)-3-iodo-salicylate

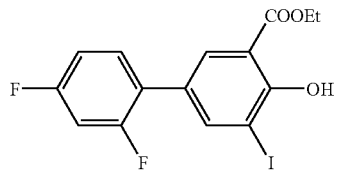

A solution of 5-(2,4-difluorophenyl)-3-iodo-salicylic acid (1.69 g, 4.61 mmol) in ethanol (20 ml) was cooled to 0° C. and a flow of anhydrous hydrochloride gas was bubbled through for 5 min. The solution was heated under reflux for 4 hr and cooled to room temperature, the solvents were evaporated at low pressure. The residue was dissolved in dichloromethane and the product was worked up. The reaction crude was purified by chromatography on silica gel using hexane/ethyl acetate (7:3) as the eluent.

Example 11 methyl 5-(2,4-difluorophenyl)-3-iodo-salicylate

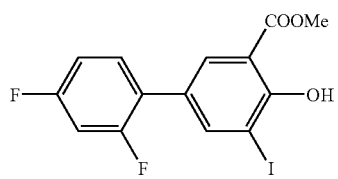

11.5 ml of methanol and 2.9 ml of thionyl chloride ($SOCl_2$) were placed in a flask under an inert atmosphere. It was stirred for 15 min and 1.67 g (4.56 mmol) of 5-(2,4-difluorophenyl)-3-iodo-salicylic acid was added. It was stirred continuously at room temperature until no evolution was observed by HPLC. The solvent was evaporated at low pressure and extraction was carried out with ethyl acetate. A crude of 97% purity was obtained and then purified by chromatography on silica gel.

Example 12

5-(2,4-difluorophenyl)-3-iodo-salicylamide

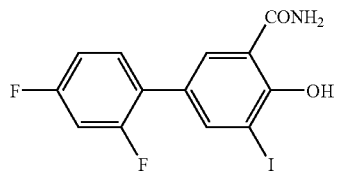

1 g (2.66 mmol) of 5-(2,4-difluorophenyl)-3-iodo-salicylic acid was mixed with 0.738 g (4.01 mmol) of pentafluorophenol in 20 ml of acetonitrile. 10 ml of N,N-diisopropylcarbodiimide was added at 0° C. and it was stirred continuously. 0.634 g of ammonium bicarbonate was dissolved in water. Consumption of the starting product was confirmed by HPLC and the crude was diluted with water and extracted with dichloromethane. The organic phase was dried over magnesium sulphate and purified on a silica gel column, using chloroform and methanol as eluents, in increasing polarity beginning with a proportion (v/v) of (40:1) up to (10:1).

Example 13

Tert-butyl [2-aminocarbonyl-4-(2,4-difluorophenyl)-6-iodo-phenoxy]-acetate

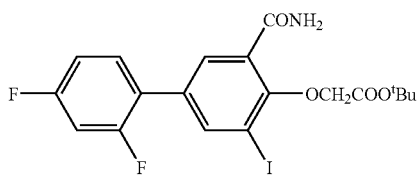

Tert-butyl chloroacetate (1.2 g, 0.008 mmol) was added to a suspension of cesium carbonate (10.4 g, 0.032 mmol) and 2.4 g (0.0064 mol) of the amide 5-(2,4-difluorophenyl)-3-iodo-salicylamide in 50 ml of DMF. The reaction was stirred for 30 min at room temperature and it was poured over a cold solution of 1 N hydrochloric acid and it was extracted with ethyl acetate. The organic phases were combined and dried over magnesium sulphate. After removing the solvent by low-pressure evaporation, a crude was obtained and then purified by flash chromatography on silica gel. The desired derivative was obtained with a 90% yield.

Example 14

[2-aminocarbonyl-4-(2,4-difluorophenyl)-6-iodo-phenoxy]acetic acid

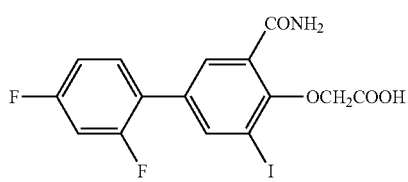

Method A:

It was obtained by reacting the ester of example 13 with trifluoroacetic acid. After stirring for a few minutes at room temperature, the residual trifluoroacetic acid was evaporated in a flow of nitrogen and it was extracted with ethyl acetate.

Method B

It was obtained by hydrolyzing the ester of example 13, in this case with hydrochloric acid. The ester (400 mg, 0.817 mmol) was dissolved in 40 ml of 50% mixture (v/v) of isopropanol and THF. 2 ml of a solution of 1 N HCl was added. The reaction was stirred for 2 hr at room temperature. It was diluted with water and extracted with ethyl acetate.

Example 15

5-(2,4-difluorophenyl)-3-iodo-salicylic acid 1-O-β-Glycoside

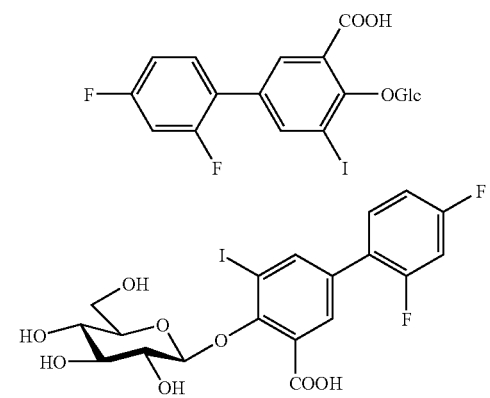

506 μl (4 mmol) of a solution of the boron trifluoride etherate ($BF_3.Et_2O$) complex in dichloromethane was drop-wise added at −40° C. under a nitrogen atmosphere to a solution of 200 mg (0.80 mmol) of the phenolic compound, 5-(2,4-difluorophenyl)-3-iodo-salicylic acid, and of 985 mg (2 mmol) of 2,3,4,6-tetra-O-acetyl-glycopyranosyl 1-trichloro-acetimidate in dichloromethane. The mixture was stirred until no starting product was observed by TLC (thin-layer chromatography). The excess of $BF_3.Et_2O$ was quenched with sodium bicarbonate. It was diluted with dichloromethane and washed with water. The organic phase was dried over magnesium sulphate and the solvent was removed at low pressure. The end product was purified by chromatography on silica gel. The protected derivative was then subjected to saponification in methanol with a catalytic quantity of sodium methoxide (Zemplen's reaction). The reaction was cold-acidified once finished it and extraction was carried out with dichloromethane. The product was then worked up in the usual way.

Example 16

Ethyl 2',4'-difluoro-4-methoxy-5-iodo-[1,1']biphenyl-3-carboxylate

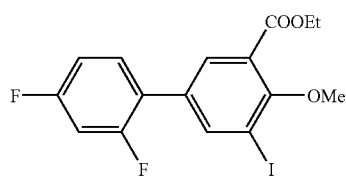

Step 1—Preparation of ethyl 2',4'-difluoro-4-methoxy-[1,1']biphenyl-3-carboxylate

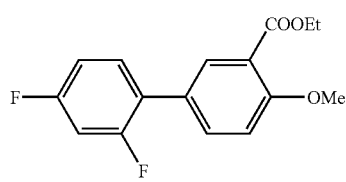

Method A

This biphenylic compound was prepared by means of a Suzuki cross-coupling reaction catalysed by Pd(0) from the corresponding boronic acid and a bromine or iodine derivative.

First of all, the bromoderivative ethyl 5-bromo-2-methoxybenzoate was prepared. This was obtained in two-step synthesis from the commercial aldehyde, 5-bromo-o-anisaldehyde, which is first treated with a permanganate solution to obtain the corresponding carboxylic acid and then esterified by in situ formation of the corresponding acid chloride by reaction with thionyl chloride and reaction with ethanol.

Suzuki's reaction: 1.15 ml (2.29 mmol, 2 eq) of a 2 N aqueous solution of sodium carbonate and 17 mg (0.111 mmol, 0.096 eq) of the Pd(0) catalyst, tetrakis(triphenyl)phosphine palladium (0), and lastly, 300 mg (1.16 mmol) of the bromoderivative (ethyl 5-bromo-2-methoxybenzoate) were added to a solution in dioxane of 190 mg (1.21 mmol, 1 eq) of 2,4-difluorophenylboronic acid. It was heated under reflux for 2 hr. It was left to cool and the catalyst was filtered through a silica gel column. It was diluted with dichloromethane and extracted with water. After the usual work-up, 330 mg of a high purity (95% by HPLC) crude was obtained.

Method B

In this case it was obtained by Williamson's reaction (preparation of asymmetric ethers) from the ethyl ester of diflunisal and methyl iodide in the presence of cesium carbonate in acetonitrile.

Step 2—Preparation of ethyl 2',4'-difluoro-4-methoxy-5-iodo-[1,1']biphenyl-3-carboxylate

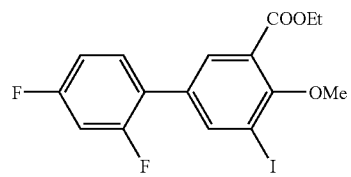

By iodination of the product obtained in step 1, ethyl 2',4'-difluoro-4-methoxy-[1,1']biphenyl-3-carboxylate, with the reagent Ipy$_2$BF$_4$ 305 mg (0.821 mmol, 1.2 eq) of bis(pyridine)iodonium (I) tetrafluoroborate (Ipy$_2$BF$_4$) was added at 0° C. to a solution of 200 mg (0.684 mmol) of ethyl 2',4'-difluoro-4-methoxy-5-iodo-[1,1']biphenyl-3-carboxylate in 5 ml of dichloromethane and 10% trifluoroacetic acid (500 µl). While being stirred, it was allowed to warm up to room temperature until the consumption of starting product was observed by HPLC. It was diluted in dichloromethane and the product was then worked up by acidification with 1 N HCl acid and extraction with dichloromethane. The organic phases were combined and washed with a solution of sodium thiosulphate and then dried over anhydrous magnesium sulphate. The solvent was removed at low pressure and a crude of 98% purity was obtained and purified by chromatography on silica gel. 260 mg (90% yield) of the desired product was obtained.

Example 17

2',4'-difluoro-4-methoxy-5-iodo-[1,1']biphenyl-3-carboxylic acid

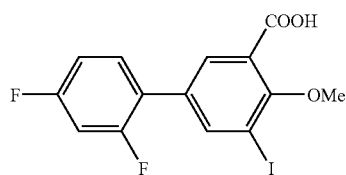

This compound was obtained by saponification of the ester of the previous example (Example 16) (ethyl 2',4'-difluoro-4-methoxy-5-iodo-[1,1']biphenyl-3-carboxylate). The ester (200 mg, 0.48 mmol) was dissolved in 20 ml of ethanol and a 2.5 N solution of NaOH for 2 hr. After cooling, the mixture was acidified with hydrochloric acid and extracted with dichloromethane. After the work-up, a crude was obtained that was recrystalized from a chloroform/hexane mixture.

Example 18

Ethyl 2',4'-difluoro-4-acetyloxy-5-iodo-[1,1']biphenyl-3-carboxylate

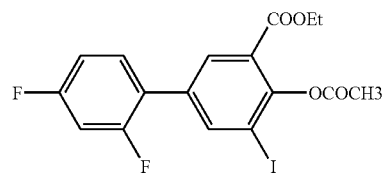

A mixture of 500 mg (1.24 mmol) of ethyl 5-(2,4-difluorophenyl)-3-iodo-salicylate (Example 10) in 12 ml of pyridine and 3 ml of acetic anhydride was heated in a water bath for 20 min. The mixture was allowed to cool and poured over ice and the product was extracted with dichloromethane. After drying the organic phase and after evaporating the solvent at low pressure, the crude was recrystalized.

Example 19

2',4'-difluoro-4-(t-butylcarbonyloxy)-5-iodo-[1,1'] biphenyl-3-carboxylic acid

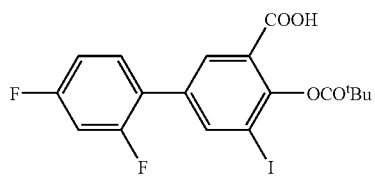

0.928 g (0.0067 mmol) of n-butyl chloroformate was added to a mixture of 2.5 g (0.0061 mmol) of 5-(2,4-difluorophenyl)-3-iodo-salicylic acid in 6 ml of benzene and 1.728 g (0.014 mmol) of dimethylaniline. The mixture was stirred at room temperature for 3 hr. Ice and a 2.5 N solution of HCl were added. It was extracted with dichloromethane and the organic phase was dried over magnesium sulphate. The solvent was evaporated at low pressure and the crude was recrystalized from a chloroform/hexane mixture.

Example 20

2',4'-difluoro-4-(ethylcarbonyloxy)-5-iodo-[1,1'] biphenyl-3-carboxylic acid

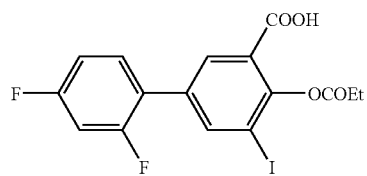

0.928 g (0.0086 mmol) of ethyl chloroformate was added to a mixture of 2.5 g (0.0061 mmol) of 5-(2,4-difluorophenyl)-3-iodo-salicylic acid in 6 ml of benzene and 1.728 g (0.014 mmol) of dimethylaniline. The mixture was stirred at room temperature for 3 hr. Ice and a solution of 2.5 N of HCl were added. It was extracted with dichloromethane and the organic phase was dried over magnesium sulphate. The solvent was evaporated at low pressure and the crude was recrystalized from a chloroform-hexane mixture.

Example 21

Ethyl ester of N-[5-(2,4-difluorophenyl)-3-iodo-salicyloyl]-glycine

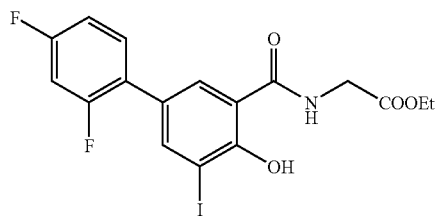

Step 1—Preparation of the ethyl ester of N-[5-(2,4-difluorophenyl)-salicyloyl]-glycine

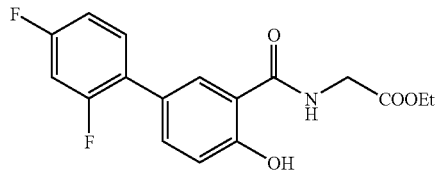

500 mg (1.998 mmol) of diflunisal and 270 mg (1.99 mmol) of HOBt dissolved in the minimum quantity of dichloromethane were placed in a flask. 206 mg (1.99 mmol) of the ethyl ester of glycine (H-Gly-OEt) was added to the mixture at room temperature and lastly 412 mg (2 mmol) of DCC (dicyclohexylcarbodiimide) dissolved in the minimum quantity of dichloromethane was added. The reaction was stirred continuously at room temperature. The process was monitored by HPLC and total consumption of the starting product was observed after one hour. The solvent was removed at low pressure and redissolved in ethyl acetate; precipitation of the corresponding urea was observed and it was then filtered. The reaction crude was purified on a silica gel column with a mixture of hexane/ethyl acetate (75:25) as the eluent. 381 mg of the desired pure product was obtained with a yield of 35%.

Step 2—Preparation of the ethyl ester of N-[5-(2,4-difluorophenyl)-3-iodo-salicyloyl]-glycine

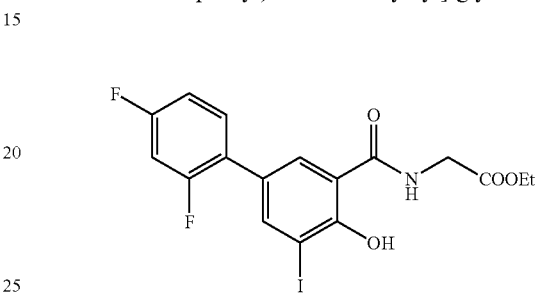

266 mg (0.715 mmol) of bis(pyridine)iodonium (I) tetrafluoro-borate ($Ipy_2BF_4$) was added at room temperature to a solution of 200 mg (0.596 mmol) of the compound of step 1 (ethyl ester of N-[5-(2,4-difluorophenyl) salicyloyl]-glycine) in 5 ml of dichloromethane. It was stirred continuously until the consumption of starting product was observed by HPLC. It was diluted in dichloromethane and the product was then worked up by acidification with 1 N HCl acid and extraction with dichloromethane. The organic phases were combined and washed with a solution of sodium thiosulphate and then dried over anhydrous magnesium sulphate. The solvent was removed at low pressure and a crude of 98% purity was obtained and then purified by chromatography on silica gel. 240 mg (87% yield) of the desired product was obtained.

Example 22

Ethyl ester of N-[5-(2,4-difluorophenyl)-3-iodo-salicyloyl]glycine

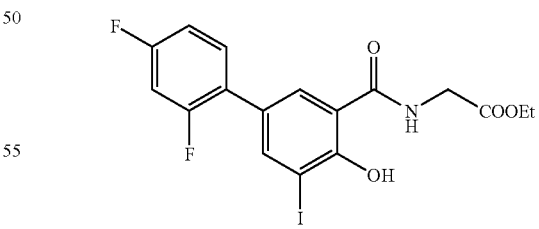

500 mg (1.32 mmol) of 5-(2,4-difluorophenyl)-3-iodo-salicylic acid (of Example 1) and 270 mg (1.99 mmol) of HOBt dissolved in the minimum quantity of dichloromethane were added to a flask. 163 mg (1.58 mmol) of the glycine ethyl ester (H-Gly-OEt) was added to the mixture at room temperature and, lastly, 272 mg (1.32 mmol) of DCC was added after being dissolved in the minimum quantity of dichloromethane. The reaction was stirred continuously at room temperature. The process was monitored by HPLC and the total consumption of the starting product was observed after one hour. The solvent was removed at low pressure and it was redissolved in ethyl acetate precipitating the corresponding urea that was then filtered. The reaction crude was purified on a silica gel column with a mixture of hexane/ethyl acetate (75:25) as the eluent. 400 mg (75% yield) of desired pure product was obtained.

Example 23

N-[5-(2,4-difluorophenyl)-3-iodo-salicyloyl]glycine

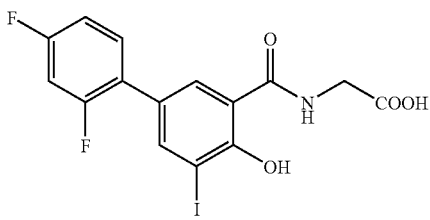

Lithium hydroxide (0.038 mg, 0.92 mmol) was added to a solution of the ester of Example 22 (480 mg, 1.19 mmol) in 5 ml of aqueous dioxane (v/v 1:1) and it was stirred under a nitrogen atmosphere for 12 hr. The mixture is concentrated at low pressure, diluted with water (10 ml) and acidified with a 0.5 M solution of hydrochloric acid and extracted with ethyl acetate. The organic phase were combined and then washed with sodium chloride saturated water and dried over sodium sulphate. The solvent was removed at low pressure and a crude of 98% purity was obtained and then purified by chromatography on silica gel.

Example 24

N-[5-(2,4-difluorophenyl-3-iodo-salicyloyl]glycine

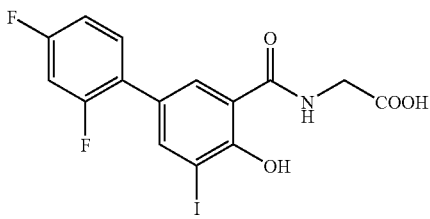

0.124 g (0.31 mmol) of pure product (ester of Example 22) was dissolved in a ternary mixture (THF:MeOH:H$_2$O) (3:1:1) and 0.1 N aqueous solution of LiOH was dropwise added to it at 0° C. It was then left at room temperature for 20 min. After the reaction finished, it was acidified with 1 N HCl to pH=2, and extracted three times with ethyl acetate and chloroform. The organic phases were combined and then washed with sodium chloride saturated water and dried over sodium sulphate. The solvent was removed at low pressure and a crude of 98% purity was obtained and then purified by chromatography on silica gel.

Example 25

N-[5-(2,4-difluorophenyl)-3-iodo-salicyloyl]alanine

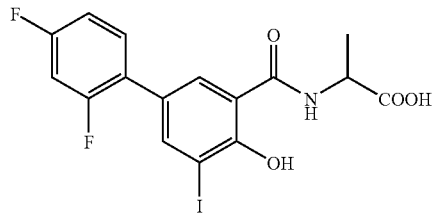

Starting from the methyl ester precursor (obtained by a method analogous to that described in Example 22 starting from alanine ethyl ester) by saponification, as described in Example 23 or in Example 24.

Example 26

N-[5-(2,4-difluorophenyl)-3-iodo-salicyloyl]-leucine

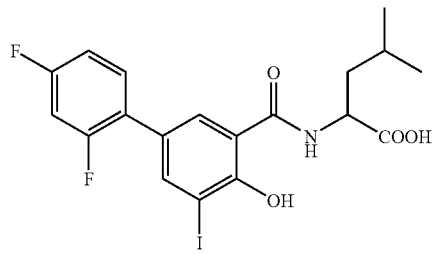

Starting from the methyl ester precursor (obtained by a method analogous to that described in Example 22 starting from the leucine ethyl ester) by saponification, as described in Example 23 or in Example 24.

Example 27

N-[5-(2,4-difluorophenyl)-3-iodo-salicyloyl]-serine

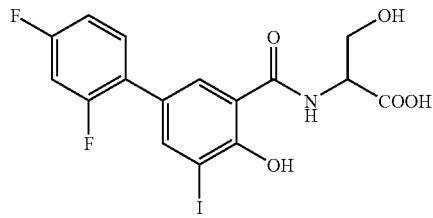

Starting from the methyl ester precursor (obtained by a method analogous to that described in Example 22 starting from the serine ethyl ester) by saponification, as described in Example 23 or in Example 24.

Example 28

N-[5-(2,4-difluorophenyl)-3-iodo-salicyloyl]-valine

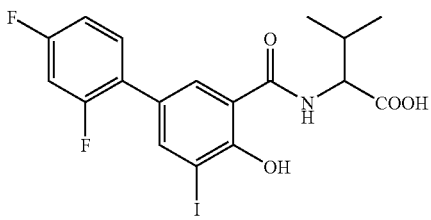

Starting from the methyl ester precursor (obtained by a method analogous to that described in Example 22 starting from the valine ethyl ester) by saponification, as described in Example 23 or in Example 24.

Example 29

N-[5-(2,4-difluorophenyl)-3-iodo-salicyloyl]-aspartic acid

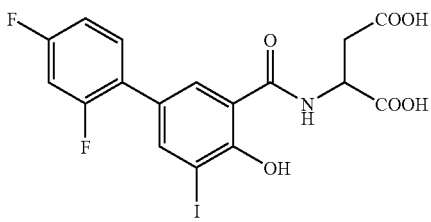

Starting from the methyl ester precursor (obtained by a method analogous to that described in Example 22 starting from the aspartic acid ethyl ester) by saponification, as described in Example 23 or in Example 24.

Example 30

N-[5-(2,4-difluorophenyl)-3-iodo-salicyloyl]-asparagine

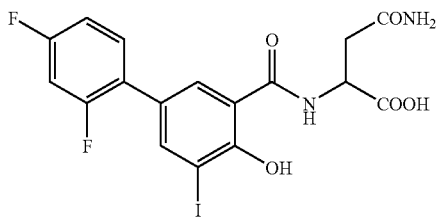

Starting from the methyl ester precursor (obtained by a method analogous to that described in Example 22 starting from the asparagine ethyl ester) by saponification, as described in Example 23 or in Example 24.

Example of Activity

Test of Amyloidogenesis Inhibiting Activity In Vitro.

The compounds of this invention had been evaluated in a turbidimetric test, whose main features were as follows:

1) use of highly amyloidogenic Y78F mutant (tyrosine78 replaced by phenylalanine) in order to boost sensitivity;
2) kinetic test monitoring fibril formation (by increased absorbance at 340 nm with time) for 1 hr 30 min to determine the initial rate of fibril formation;
3) test format in 96-well microplates for quick analysis of a number of samples at the same time at different inhibitor concentrations;
4) calculation of the inhibition parameters of every inhibitor on the basis of the initial fibril formation rate curves versus inhibitor concentration.

Protocol:

The compounds to be tested as inhibitors were dissolved in DMSO at a concentration of 1.5 mM. The working solution was prepared by 1 to 4 dilution of the previous solution in a water/DMSO mixture (2:1). The protein solution (Y78F hTTR mutant) was 4 mg/ml of protein (purity higher than 95%) in 20 mM sodium phosphate, 100 mM potassium chloride, pH 7.6. The incubation buffer was 10 mM sodium phosphate, 100 mM potassium chloride, 1 mM EDTA, pH –7.6. The dilution buffer was 400 mM sodium acetate, 100 mM potassium chloride, 1 mM EDTA, pH 4.2. The test protocol for an inhibitor was as follows: 20 µl of the protein solution was dispensed in 7 wells of a 96-well microplate. Different volumes of the inhibitor working solution were added to each of the wells to obtain end concentrations of 0 to 40 µM. Incubation buffer was then added to each well up to an end volume of 100 µl. The microplate was incubated at 37° C. in the microplate reader provided with thermostatting and stirring. Incubation proceeded for 30 min at 37° C. with stirring for 15 seconds every minute. 100 µl of dilution buffer was then added to every well, and the mixture was incubated at 37° C. with stirring for 15 seconds every minute in the microplate reader and absorbance was monitored at 330 nm for 1 hour 30 minutes at intervals of 1 minute. The data of absorbance versus time for every well were collected and analysed with the Microsoft Excel program. All tests were done in duplicate.

Calculations:

1.—Initial fibril formation rate. From the absorbance readings at 330 nm with the incubation time for every well, the initial fibril formation rate was calculated as the slope of the initial linear portion of the curve. Thus, the aggregation rate was obtained at every inhibitor concentration.

2.—Aggregation rate versus inhibitor concentration. Aggregation rates versus inhibitor concentration followed an exponential decay that conformed to the equation:

$$v_0 = A + B \cdot e^{-C[I]}$$

where $v_0$ was the aggregation rate (in units of absorbance per hour) and $[I]$ was the inhibitor concentration in µM.

FIG. 1 shows that variation in the aggregation rate, $v_0$, in relation to inhibitor concentration, $[I]$, for a compound of the invention, iododiflunisal, versus two compounds of the state of the art, diflunisal and diflunisal ester.

The adjusted parameters were: A (in units of absorbance per hour), residual aggregation rate at high inhibitor concentration; B (in units of absorbance per hour), amplitude or maximum reduction of the aggregation rate; and C (in µM$^{-1}$) the exponential constant. A+B was the aggregation rate in the absence of inhibitor (maximum aggregation rate). From these parameters, other parameters were extracted that characterised every inhibitor with regard to its capacity and effectiveness in inhibiting fibril formation:

$IC_{50}$: inhibitor concentration (μM) at which the aggregation was half that in the absence of inhibitor;

$\Psi$: initial slope of curve $v_0$ versus [I], which reflected the sensitivity of the aggregation process to the inhibitor. The higher the values of $\Psi$, the greater the inhibiting effect of the compound at initial fibril formation times;

$RA(\%)=(1-A/(A+B))\cdot 100$: % reduction of the rate of aggregation at high inhibitor concentration compared with the rate in the absence of inhibitor.

In accordance with this test, a good inhibitor is one that presents a low $IC_{50}$, a high $\Psi$ value, and an RA value (%) close to 100%.

The results are shown in Table 1. It sets out the values of the above-mentioned parameters for iodinated and non-iodinated diflunisal and its derivatives. As may be seen, the iodinated compounds present a clearly enhanced activity compared with non-iodinated compounds.

TABLE 1

Diflunisal and derivatives: effect of iodination

| Inhibitor | Structure | $IC_{50}$ (μM) | $\Psi$ (UA · hr$^{-1}$ · μM$^{-1}$) | RA (%) |
|---|---|---|---|---|
| Diflunisal | 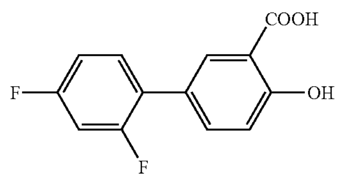 | 12.9 | 0.036 | 84 |
| Iododiflunisal | 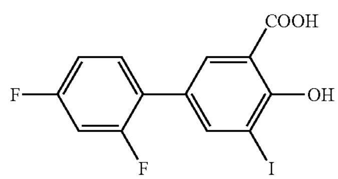 | 4.5 | 0.100 | 97 |
| Diflunisal methyl ester | 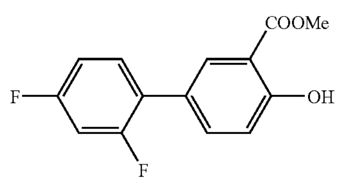 | >100 | 0.011 | 24 |
| Iododiflunisal methyl ester | 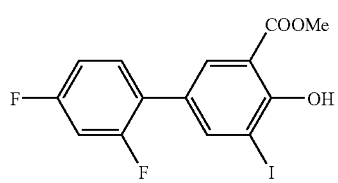 | 16.7 | 0.027 | 98 |
| Diflunisal amide | 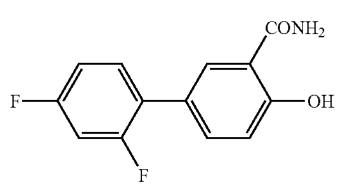 | >100 | 0.009 | 10 |
| Iododiflunisal amide | 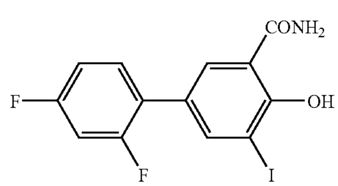 | 11.7 | 0.041 | 84 |
| Diflunisal glycine | 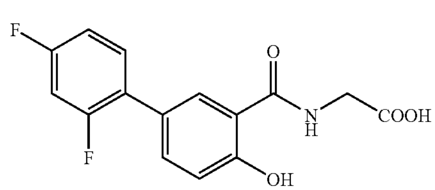 | >100 | 0.011 | 28 |

TABLE 1-continued

Diflunisal and derivatives: effect of iodination

| Inhibitor | Structure | $IC_{50}$ (μM) | Ψ (UA · hr$^{-1}$ · μM$^{-1}$) | RA (%) |
|---|---|---|---|---|
| Iododiflunisal glycine | 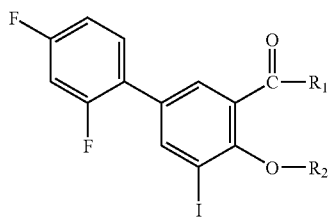 | 11.2 | 0.040 | 100 |

The invention claimed is:

1. A compound of structural formula (I):

(I)

in which
R$_1$ is a —NR$_a$R$_b$ group, where R$_a$ and R$_b$, independently, are a hydrogen atom or a C$_1$-C$_6$ alkyl group; —OR$_C$ group, where R$_C$ is a hydrogen atom or a C$_1$-C$_6$ alkyl group; a glycosyl; a C$_1$-C$_6$ polyhydroxyalkyl; or a —NH—CH(R$_d$)—COOR$_e$ group, where R$_d$ is a side chain of one of the 20 natural alpha-amino acids in either of their two enantiomerically pure forms L or D, and R$_e$ is a hydrogen atom or a C$_1$-C$_6$ alkyl group; and
R$_2$ is a hydrogen atom, a C$_1$-C$_6$ alkyl group, a glycosyl; a C$_1$-C$_6$ polyhydroxyalkyl; —C(=O)—R$_f$ group, where R$_f$ is a C$_1$-C$_6$ alkyl group; or a —CH$_2$—COO—R$_g$ group, where R$_g$ is a hydrogen atom or a C$_1$-C$_6$ alkyl group;
and pharmaceutically acceptable salts thereof.

2. A compound according to claim 1, wherein R$_1$ is selected from: OH, NH$_2$, OMe, OEt, or a CH(R$_d$)—COR$_e$ group, where R$_d$ is the side chain of glycine, alanine, leucine, valine, aspartic acid or asparagine and where R$_e$ is H or a C$_1$-C$_6$ alkyl group; and R$_2$ is selected from: H, Me, glycosyl, a —C(=O)—R$_f$ group, where R$_f$ is a Me, Et, t-Bu group; or a —CH$_2$—COO—R$_g$ group, where R$_g$ is a hydrogen atom or a t-Bu group.

3. A compound according to claim 1, selected from the group consisting of:
[1] 5-(2,4-difluorophenyl)-3-iodo-salicylic acid;
[2] ethyl 5-(2,4-difluorophenyl)-3-iodo-salicylate;
[3] methyl 5-(2,4-difluorophenyl)-3-iodo-salicylate;
[4] 5-(2,4-difluorophenyl)-3-iodo-salicylamide;
[5] tert-butyl [2-aminocarbonyl-4-(2,4-difluorophenyl)-6-iodo-phenoxy]-acetate;
[6] [2-aminocarbonyl-4-(2,4-difluorophenyl)-6-iodo-phenoxy]acetic acid;
[7] 5-(2,4-difluorophenyl)-3-iodo-salicylic acid 1-O-β-glycoside;
[8] ethyl 2',4'-difluoro-4-methoxy-5-iodo-[1,1']biphenyl-3-carboxylate;
[9] 2',4'-difluoro-4-methoxy-5-iodo-[1,1']biphenyl-3-carboxylic acid;
[10] ethyl 2',4'-difluoro-4-acetyloxy-5-iodo-[1,1']biphenyl-3-carboxylate;
[11] 2',4'-difluoro-4-(t-butylcarbonyloxy)-5-iodo-[1,1']biphenyl-3-carboxylic acid;
[12] 2',4'-difluoro-4-(ethylcarbonyloxy)-5-iodo-[1,1']biphenyl-3-carboxylic acid;
[13] ethyl ester of N-[5-(2,4-difluorophenyl)-3-iodo-salicyloyl]glycine;
[14] N-[5-(2,4-difluorophenyl)-3-iodo-salicyloyl]glycine;
[15] N-[5-(2,4-difluorophenyl)-3-iodo-salicyloyl]alanine;
[16] N-[5-(2,4-difluorophenyl)-3-iodo-salicyloyl]leucine;
[17] N-[5-(2,4-difluorophenyl)-3-iodo-salicyloyl]serine;
[18] N-[5-(2,4-difluorophenyl)-3-iodo-salicyloyl]valine;
[19] N-[5-(2,4-difluorophenyl)-3-iodo-salicyloyl]-aspartic acid and;
[20] N-[5-(2,4-difluorophenyl)-3-iodo-salicyloyl]asparagine.

4. A method for the preparation of a compound of formula (I) according to claim 1, comprising a step of reacting diflunisal or at least one derivative thereof with an iodination reagent.

5. A method according to claim 4, wherein the iodination reagent is selected from the group consisting of: elemental iodine; iodide salts; sodium iodide; potassium iodide; iodonium salts; iodine chloride; iodonium complexes; bis(pyridine)iodonium (I)tetrafluoroborate; bis(symcollidine)iodonium (I) hexafluorophosphate; organic iodine compounds; iodobenzene diacetate; and N-iodosuccinimde.

6. A pharmaceutical composition containing a compound according to claim 1 and one or more pharmaceutically acceptable excipients.

* * * * *

UNITED STATES PATENT AND TRADEMARK OFFICE
CERTIFICATE OF CORRECTION

PATENT NO. : 7,265,245 B2
APPLICATION NO. : 10/574875
DATED : September 4, 2007
INVENTOR(S) : Mascarenhas Saraiva et al.

It is certified that error appears in the above-identified patent and that said Letters Patent is hereby corrected as shown below:

Cover page, Inventors, second line, "Oporto (PT)" should be -- Porto (PT)--.

Cover page, Inventors, third line, "Oporto (PT)" should be -- Porto (PT)--.

Column 20, line 22, "pH -7.6" should be -- pH 7.6 --.

Signed and Sealed this

Eighteenth Day of December, 2007

JON W. DUDAS
*Director of the United States Patent and Trademark Office*